United States Patent [19]
Ventura

[11] Patent Number: 5,818,593
[45] Date of Patent: Oct. 6, 1998

[54] FLAW HIGHLIGHTING LIGHT PANEL LENS

[75] Inventor: George Ventura, Bonner Springs, Kans.

[73] Assignee: It's Dents Or Us, Inc., Overland Park, Kans.

[21] Appl. No.: 851,374

[22] Filed: May 5, 1997

Related U.S. Application Data

[63] Continuation-in-part of Ser. No. 432,797, May 2, 1995, Pat. No. 5,675,417, which is a continuation-in-part of Ser. No. 247,640, May 23, 1994, Pat. No. 5,436,726.

[51] Int. Cl.$^6$ ............................................. G01N 21/00
[52] U.S. Cl. ........................................ 356/371; 356/237
[58] Field of Search .................................. 356/237, 371; 250/462.1, 467.1

[56] References Cited

U.S. PATENT DOCUMENTS

| | | |
|---|---|---|
| 1,566,636 | 1/1925 | Schulz . |
| 1,568,954 | 1/1926 | Boedtcher . |
| 4,448,527 | 5/1984 | Milana ..................... 356/237 |
| 4,629,319 | 12/1986 | Clarke et al. ............. 356/237 |
| 4,792,232 | 12/1988 | Jobe et al. ................ 356/394 |
| 5,090,804 | 2/1992 | Wong et al. .............. 356/237 |
| 5,168,322 | 12/1992 | Clarke et al. ............. 356/237 |
| 5,206,700 | 4/1993 | Reynolds et al. ......... 356/237 |
| 5,225,890 | 7/1993 | Lee et al. ................. 350/371 |
| 5,237,404 | 8/1993 | Tanaka et al. ............ 356/371 |
| 5,436,726 | 7/1995 | Ventura et al. ........... 356/237 |
| 5,572,324 | 11/1996 | Ventura et al. ........... 356/237 |
| 5,579,429 | 11/1996 | Naum . |
| 5,583,640 | 12/1996 | Ventura et al. ........... 356/237 |
| 5,675,412 | 10/1997 | Ventura et al. ........... 356/237 |

FOREIGN PATENT DOCUMENTS

| | | | |
|---|---|---|---|
| 269006 | 11/1988 | Japan ....................... 356/371 |
| 264448 | 10/1993 | Japan ....................... 356/371 |

OTHER PUBLICATIONS

Hugh W. Lippincott and Henry Stark; Optical–Digital Detection Of Dents And Scratches On Specular Metal Surfaces; Aug. 15, 1982; *Applied Optics*, vol. 21, No. 16, pp. 2875–2881.

Henry Pearson, Piping Lifht with Acrylic Materials, *Modern Plastics*, Aug. 1946, pp. 123–127.

Photographs of a dent highlighting panel which was in public use or on sale prior to May 23, 1993.

*Primary Examiner*—Richard A. Rosenberger
*Attorney, Agent, or Firm*—Litman, McMahon & Brown, L.L.C.

[57] ABSTRACT

An improved lens for flaw highlighting light panels having at least one light colored translucent strip adjacent at least one dark colored opaque strip and a narrow reference strip which is luminescent or of intensified light and which extends across at least a portion of the dark colored opaque strip. The characteristics of the reflected light from the luminescent or intensified light reference strip makes the reference strip stand out more than a reference strip which is not luminescent or of intensified light thereby facilitating the detection of dents.

17 Claims, 2 Drawing Sheets

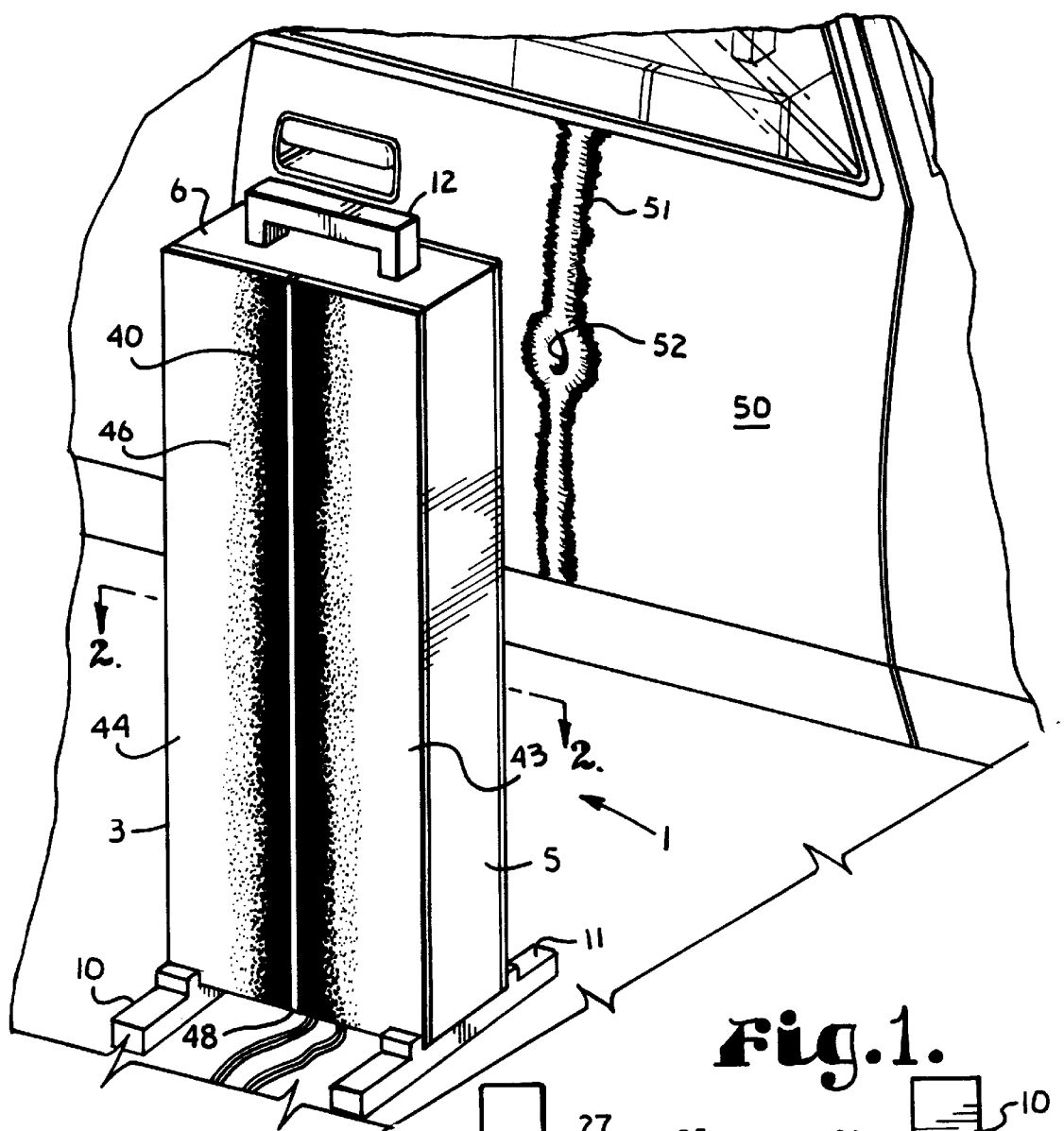
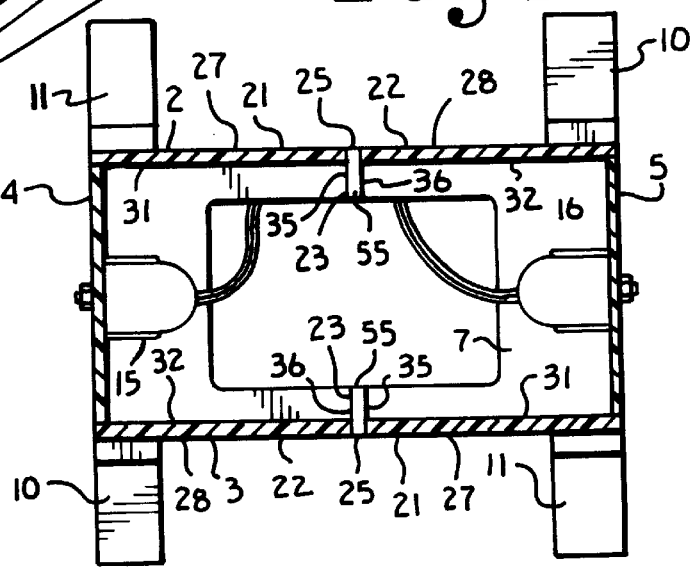

FLAW HIGHLIGHTING LIGHT PANEL LENS

This application is a continuation-in-part of application Ser. No. 08/432,797, entitled INFINITELY ADJUSTABLE AUTOMOBILE BODY REPAIR LIGHT PANEL SUPPORT, filed May 2, 1995, U.S. Pat. No. 5,675,417; which is a continuation in part of application Ser. No. 08/247,640, entitled FLAW HIGHLIGHTING LIGHT PANEL AND BOOTH FOR AUTOMOBILE BODY REPAIR, filed May 23, 1994, which issued on Jul. 25, 1995, as U.S. Pat. No. 5,436,726.

BACKGROUND OF THE INVENTION

The present invention relates to an improved lens for light panels used to highlight dents or other flaws on a surface such as the surface of an automobile body.

It is often difficult to detect small dents and other imperfections in the surface of an automobile body by unaided eyesight. This is particularly true of new or newly painted automobiles viewed under artificial light, such as in an automobile assembly plant or repair and paint shops. In such assembly plants and repair shops, it is important that even the smallest dent or imperfection be detected to provide for satisfied customers and dealers and to avoid adversely affecting the reputation of the plant or shop.

In U.S. Pat. Nos. 5,436,726 and 5,583,640, I disclosed a flaw highlighting light panel and a light panel booth for highlighting flaws on the surface of an automobile body. The panel and booth incorporate a lens mounted in front of a fluorescent light. The lens is formed from a sheet of a light colored translucent material with a black, opaque stripe or band painted across the center of the lens. A narrow centerline, strip or band on the lens is masked off when the black, opaque stripe is painted across the lens, such that when the tape is removed a narrow centerline, stripe or band of the light colored translucent material extends along the center of the black opaque stripe.

The light panel is directed toward a surface to be inspected such that the pattern of the lens is reflected on the surface. The narrow centerline serves to project a narrow centered light band in the middle of each black, opaque stripe of the pattern to function as a reference line, allowing an observer to correctly position his observation position to facilitate the observation of dents and flaws.

SUMMARY OF THE INVENTION

The present invention generally comprises an improved lens for flaw highlighting light panels having at least one light colored translucent strip adjacent at least one dark colored opaque strip and a narrow reference strip which is luminescent or of intensified light and which extends across at least a portion of the dark colored opaque strip. The characteristics of the reflected light from the luminescent or intensified light reference strip makes the reference strip stand out more than a reference strip which is not luminescent or of intensified light thereby facilitating the detection of dents.

OBJECTS AND ADVANTAGES OF THE INVENTION

The objects of the present invention include to provide an improved lens for use with flaw highlighting light panels which facilitates the detection of and repair of flaws in a surface to be inspected; to provide such a lens which includes at least one translucent light colored strip adjacent at least one opaque dark colored strip and having a relatively narrow light colored strip extending through each of said opaque dark colored strips and which stands out from the opaque dark colored strip and the translucent light colored strip; to provide such a lens in which the relatively narrow light colored strip is luminescent; to provide such a lens which is relatively easy to manufacture; to provide such a lens which is interchangeable with previously installed lenses; to provide such a lens which is particularly well adapted for its intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a portable flaw highlighting light panel incorporating improved lenses in accordance with the present invention and shown highlighting a dent on an automobile body panel.

FIG. 2 is a cross-sectional view taken along line 2—2 of FIG. 1.

DETAILED DESCRIPTION OF THE INVENTION

Figure 3:
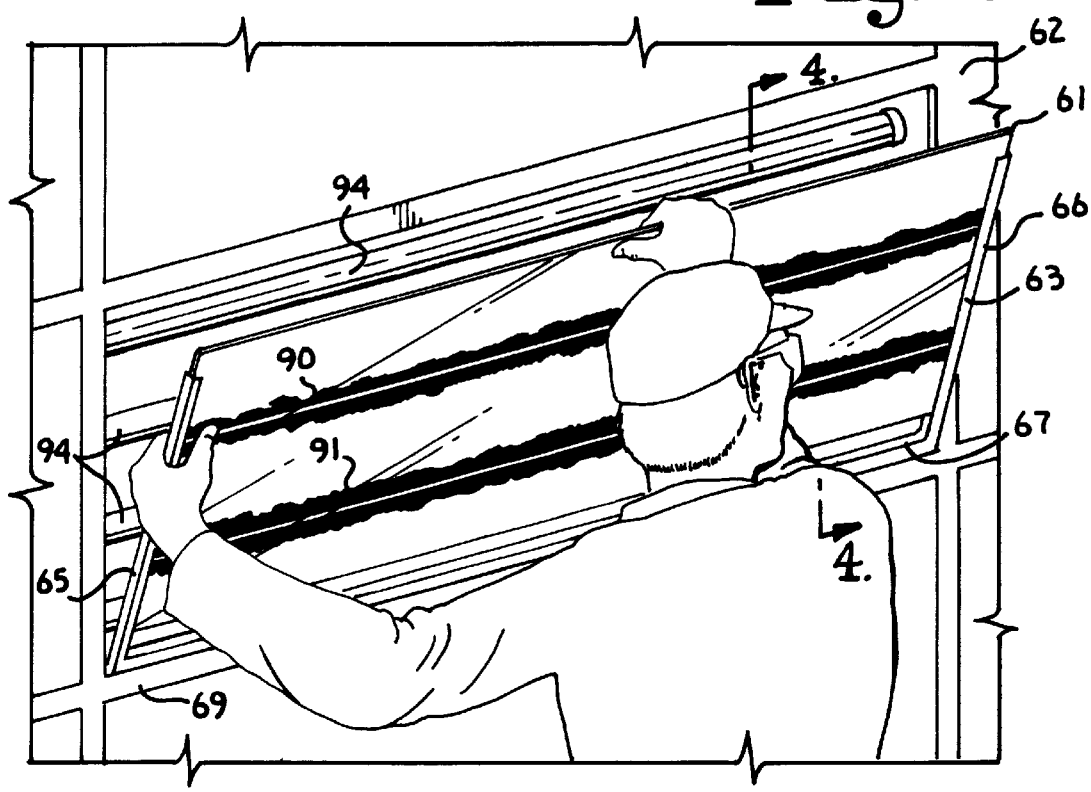
FIG. 3 is a fragmentary perspective view showing an alternative embodiment of an improved lens of the present invention being installed in a flaw highlighting light panel booth.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to FIGS. 1 and 2 in more detail, the reference numeral 1 refers to a portable flaw highlighting light panel box. The light panel box 1 includes opposite facing lenses 2 and 3, sidewalls 4 and 5, top plate 6 and bottom plate 7. The light panel box is supported on legs 10 and 11 secured to the bottom plate 7 and includes a handle 12 secured to the top plate 6. Sidewalls 4 and 5, top plate 6 and bottom plate 7 generally comprise a frame or framework of the light panel box 1. A pair of backlighting fluorescent lamps 14 and 15 are mounted on inner surfaces of sidewalls 4 and 5 and function as a light source.

Each lens 2 and 3 is formed from three pieces, sections or portions of plastic sheet material such as Plexiglas, poly (methyl methacrylate) which generally comprises an acrylic resin or acrylic plastic. The preferred embodiment utilizes acrylic sheet material which is approximately a quarter inch thick. First and second outer sections 21 and 22 of lenses 2 and 3 are formed from acrylic sheet material which has a translucent, light color preferably white and yellow as discussed in more detail below. A third, center section 23 of each lens 2 and 3 is formed from acrylic sheet material which is generally transparent having a fluorescent or luminescent dye dispersed throughout, such as fluorescent acrylic sheet material or plastic marketed as Fluorescent Plexiglas. A preferred color of the fluorescent acrylic sheet material is a yellow-green. U.S. Pat. No. 5,479,429 to Naum discloses a partial listing of fluorescent dyes which are utilized in acrylic plastics to provide luminescent properties.

The center section 23 of each lens 2 and 3 is mounted between and transverse to the first and second sections 21 and 22 of each lens 2 and 3 such that a front edge 25 of the center section 23 generally extends flush with outer surfaces 27 and 28 of first and second sections 21 and 22 respectively. The center section 23 of each lens 2 and 3 is preferably sized such that a portion thereof extends beyond and behind inner surfaces 31 and 32 of the first and second sections 21 and 22 respectively such that opposed faces 35 and 36 of the center section 23 are exposed to light from the lamps 14 and 15.

The various components of the light box 1 are generally secured together by gluing except for the lamps 14 and 15 which are bolted to the sidewalls 4 and 5 respectively. After the components of the light box are assembled, the front edge 25 of the center section 23 of each lens 2 and 3 is masked off with masking tape. Dark colored paint, preferably black, is sprayed down the center of each lens 2 and 3 to form a centered, opaque, dark colored stripe or band 40 extending between the remaining unpainted light colored portions of the first and second sections 21 and 22 of each lens 2 and 3. The unpainted light colored portions generally form light colored bands 43 and 44. The paint is sprayed onto the lenses 2 and 3 heavy toward the center and lighter toward the edges so as to bleed into the light colored bands 43 and 44, creating a wavy and indistinct shadow line 46 between the dark colored band 40 and each light colored band 43 and 44. After the dark colored band 40 is applied, the masking tape is removed to expose the front edge 25 of the center section 23 of each lens 2 and 3 such that the front edge 25 forms a narrow center line 48 or stripe extending centrally across or through the dark colored stripe 40.

In use, the light panel box 1 is positioned proximate an automobile body surface 50 such that a pattern of light 51 emitted from the light panel box 1 is reflected onto the portion of the automobile body surface 50 to be inspected. Flaws or dents in the automobile body surface 50 cause easily detectible distortions in the light pattern 51 reflected therefrom. In particular, as the portion of the light pattern 51 corresponding to the narrow center line 48 is visually moved across a dent 52 in the automobile body surface 50, the reflection of the narrow centerline 48 appears to wrap or curve around the dent thereby highlighting the location of the dent 52 for repair. The shadow line 46 is also useful in locating and determining the depth of the dent to facilitate repair.

The light colored bands 43 and 44 on the lens 2 are preferably translucent yellow while the bands 43 and 44 on the lens 3 are preferably translucent white. The yellow lens 2 is more effective for inspection of lighter colored automobiles, such as white, light gray, silver, etc. while the white lens 4 is more effective for darker colored automobiles, such as dark gray, black, brown, etc.

When the lamps 15 and 16 are turned on, the front edge 25 of the center section 23 glows and emits light which appears more intense than light emitted through the translucent light colored plastic. Use of the fluorescent acrylic plastic produces a narrow center line 48 having a reflection which appears brighter and therefore easier to observe thereby facilitating the detection and repair of flaws.

It is understood that the glow observed along the front edge 25 of the center section 23 is the result of the internal reflection, refraction and fluorescent properties of the fluorescent acrylic plastic. The fluorescent acrylic plastic utilized in the preferred embodiment contains a dye which will fluoresce through absorption of a portion of the spectrum of light emitted from standard fluorescent lights.

Light, from lamps 15 and 16 passing through the opposed faces 35 and 36 of the center section 23 (at any angle other than a right angle with the surface), is refracted toward a line extending perpendicular with the surface. As the angle of incidence with respect to the perpendicular increases, the angle of refraction also increases. The critical angle for light passing from air through an acrylic plastic is approximately 42.2 degrees which corresponds to the angle at which light striking the acrylic plastic at an angle practically parallel to the surface of the plastic enters the acrylic plastic relative to the perpendicular.

Conversely, any ray of light in the acrylic plastic which hits an outer surface in contact with air at an angle greater than 42.2 degrees with the perpendicular cannot escape but is reflected from the surface internally and rebounds at an equal and opposite angle within the plastic. Where the two surfaces of the acrylic plastic are parallel, as with the center section 23, the internally reflected rays rebound from one surface to the other advancing lengthwise through the material.

It is understood that when the dye in the fluorescent plastic fluoresces it emits light at an angle of 90 degrees relative to the angle of incidence of the absorbed light or radiation. Whereas any light entering the central section 23, through opposed faces 35 and 36, does so at or below the critical angle, the fluorescent light, resulting from the portion of the light which is absorbed by the dye, is generally emitted such that the angle of incidence of the emitted fluorescent light with the opposed face 35 or 36 is at or above the critical angle causing internal reflection of the resultant fluorescent light along the length of the central section 23.

When the internally reflected fluorescent light reaches the front edge 25 or a rear edge 55 thereof, the angle of incidence therewith is below the critical angle, allowing the fluorescent light to escape therethrough, such that the front edge 25 appears to glow. The further the central section extends into the internal portion of the light panel box 1, the brighter or more intense the fluorescent light emitted at the front edge 25 appears because of the increase in the amount of fluorescent material and the corresponding increase of fluorescent light emitted thereby.

Although abutment of the ends of the first and second sections 21 and 22 of each lens 2 and 3 against the respective central section 23 will change the angle of refraction of the light thereacross, it is not believed that any significant loss of light therethrough occurs and most if not all of the fluorescent light is guided out the front edge 25 through internal reflection.

The central section 23 generally functions as an optical wave guide, concentrating and directing light to the front edge 25 thereof. Because of this optical effect, the narrow center line 48 of each lens 2 and 3 stands out in sharp contrast to the dark stripe 40 and displays a fluorescent glow.

The reflection of the narrow center line 48 is therefore more visually perceptible on the automobile body surface 50 than in previous embodiments.

FIGS. 3 through 6 show an alternative embodiment of a lens 61 of the present invention adapted for use in a flaw highlighting light panel booth 62, such as disclosed in U.S. Pat. Nos. 5,436,726 and 5,583,640. The lens 61 is adapted for use with a lens support frame 63 typical of conventional fluorescent light fixtures. The lens support frame 63 generally comprises four C-channel members; end channel members 65 and 66, bottom channel member 67 and top channel member 68 which is not shown. The lens support frame 63 is shown in FIG. 3 hingedly secured to frame member 69 of the booth 62 and with the top channel member 68 removed to permit insertion of the lens 61 therein.

Figure 4:
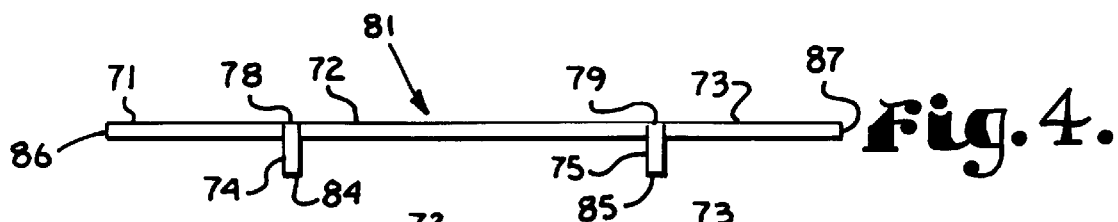
FIG. 4 is an enlarged cross-sectional view of the lens shown in FIG. 3 taken along line 4—4 thereof.
Figure 5:
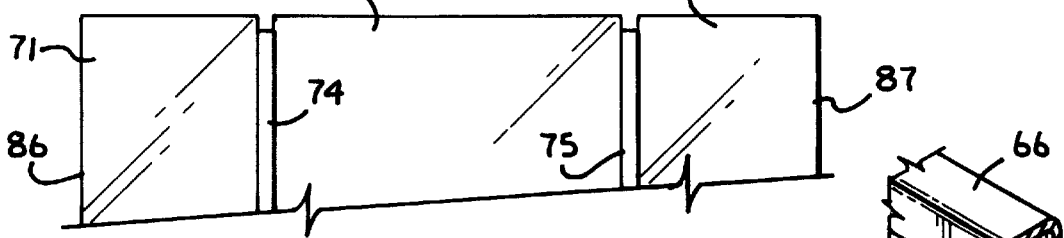
FIG. 5 is a fragmentary view of the lens shown in FIG. 4 taken generally along line 5—5 thereof.
Figure 6:
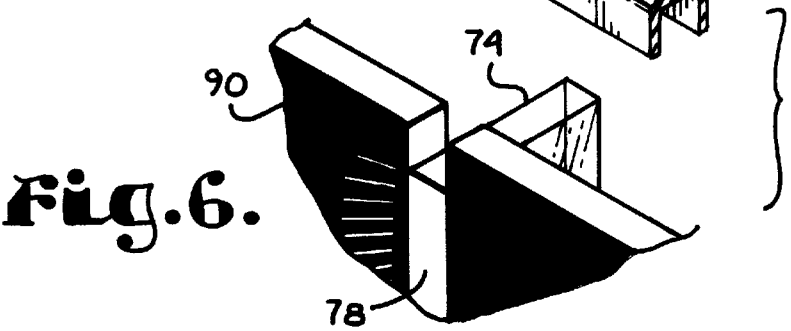
FIG. 6 is an enlarged, fragmentary and exploded front perspective view of an end of the lens as shown in FIG. 3 rotated ninety degrees relative thereto.

The lens is formed from five sections of acrylic sheet material including: first, second and third face sections 71, 72 and 73 and first and second rearwardly projecting intermediate sections 74 and 75 which are secured between the face sections 71, 72 and 73 as generally shown in FIG. 4. Front edges 78 and 79 of rearward projecting sections 74 and 75 extend flush with a front face 81 of the lens 61.

The rearwardly projecting sections 74 and 75 are shorter than the face sections 71, 72 and 73 and secured therebetween such that ends 84 and 85 of the rearwardly projecting sections 74 and 75 are spaced inward from ends 86 and 87 of the lens 61. The inward spacing of ends 84 and 85 of rearwardly projecting sections 74 and 75 is shown for one end 86 of the lens 61 in FIGS. 5 and 6. The opposite end 87 is of similar construction. Inward spacing of the rearwardly projecting sections 74 and 75 allows the ends 86 and 87 of lens 61 to be slidingly secured within the end channel members 65 and 66 of the lens support frame 63 to support the lens thereby.

The rearwardly projecting sections 74 and 75 are formed from fluorescent acrylic plastic as discussed above and the face sections 71, 72 and 73 are formed from a translucent light colored (preferably yellow or white) plastic sheet material. Dark colored opaque stripes or bands 90 and 91 are applied to the lens 61 generally in the manner discussed above for lenses 2 and 3, with each dark colored opaque band 90 and 91 centered on a respective rearwardly projecting section front edge 78 and 79, which is masked off during the painting process. The edges of the dark colored opaque bands 90 and 91 are applied so as to be wavy and indistinct as with lenses 2 and 3.

The lens support frame 63 supports the lens 61 across a fluorescent light fixture 90 which incorporates a plurality of fluorescent lights 94 to backlight the lens. The optical properties of the rearwardly projecting sections 74 and 75 result in the emission of a narrow center line or band of relatively bright fluorescent light as discussed with respect to lenses 2 and 3 which facilitates the detection of dents.

It is foreseen that a wide variety of means could be utilized to produce a narrow centerline which stands out or appears relatively bright. For example, it is foreseen that the lenses could be made from a single sheet of fluorescent acrylic plastic with a V-shaped or U-shaped groove formed on an inner surface of each lens behind the narrow center line which is masked off during painting of the dark stripe or band on an outer surface of each lens. Internally reflected fluorescent light striking the surface of the V-shaped groove is reflected therefrom at an angle which permits escape of the light through the outer surface of the lens thereby producing a fluorescent glow. Abrading or painting the inner surface of such a lens opposite the portion masked off to form the narrow centerline should also make the centerline appear to glow. In such an embodiment the portion of the rear or inner surface behind the dark strip may also need to be painted to enhance the brightness or glow created by the groove.

It is foreseen that a similar effect could be obtained through painting a sheet of clear plexiglass with appropriate light, dark and fluorescent paint to form a lens. For example such a lens could be made by first applying a band of fluorescent paint down the center of the sheet and then masking off a narrow band of the fluorescent paint with a strip of masking tape corresponding to the width of the desired narrow centerline. A coating of a light colored paint, preferably white or yellow, could then be applied across the entire sheet in a light enough coating to generally be translucent when backlit. A band of dark colored paint could then be applied down the center of the sheet in accordance with the method disclosed above for the preferred embodiment. The strip of masking tape is then removed to reveal a narrow centerline of fluorescent paint which would appear to glow when backlit. In an alternative embodiment utilizing light, dark and fluorescent colored paints on clear plastic sheets, the paint could be applied in a similar fashion but on the face of the plastic sheet comprising the inner surface of the lens, and the fluorescent paint would be applied in a groove formed down the center of the sheet which may enhance the glowing effect.

It is also foreseen that alternative optical wave guide means could be utilized to generally guide light from a lamp or light source for emission along a narrow center line or band on a front face of the lens. For example, it is foreseen that such a light panel apparatus could incorporate a lens formed from three sections of acrylic plastic as generally disclosed for the preferred embodiment noted above except with the center section formed from clear acrylic plastic. A fluorescent bulb would be mounted behind and in close proximity to a rear edge of the center section of the lens. The center section would function as an optical wave guide, guiding the light entering the rear edge of the center section out the front edge thereof with minimal loss thereby producing a relatively bright narrow center line or band of light in contrast to the light emitted from the translucent backlit portions of the lens. It is foreseen that a wide range of configurations of such optical wave guides could be utilized.

It is also foreseen that similar results could be obtained through utilization of edge lighting. For example, a sheet of clear acrylic plastic having a V-shaped groove down the center of a back surface thereof which is lit along the side edges will produce a narrow band of light along the groove when viewed from the front. Painting the surface of the groove with fluorescent paint or passing the light through a colored lens along the side edges can be used to produce a fluorescent or colored band of light along the groove.

It is foreseen that phosphorescent materials might be substituted for fluorescent materials to produced the desired results. Further, although the light source of the present invention comprises fluorescent lamps it is foreseen that alternative light sources might be utilized including incandescent lamps, black light lamps or other suitable light sources.

It is also foreseen that the lenses of the present invention could be used with a wide variety of flaw highlighting light panel apparatus including smaller portable units or in existing fluorescent light fixtures.

It is to be understood that while certain forms of the present invention have been illustrated and described herein, it is not to be limited to the specific forms or arrangement of parts described and shown.

What is claimed and desired to be secured by Letters Patent is as follows:

1. A lens for use in association with a light source to inspect a surface for imperfections; said lens including:
   a) a pattern having a light colored area adjacent a dark colored area, and a luminescent strip extending at least partially through said dark colored area; said lens projecting light from said light source in said pattern onto said surface to be inspected when said lens is facing said surface to highlight flaws and imperfections in said surface.

2. The lens as in claim 1, wherein:
   a) said lens is mounted to a framework in front of said light source.

3. The lens as in claim 1, wherein:
   a) said dark colored area bleeds into said light colored area.

4. The lens as in claim 1, wherein:
   a) said light colored area is translucent; and
   b) said dark colored area is opaque.

5. A lens for use in association with a light source to inspect a surface for imperfections; said lens including:
   a) a pattern having a light colored area adjacent a dark colored area; and
   b) an optical wave guide guiding light from said light source and producing a narrow band of light in said pattern extending at least partially through said dark colored area of said pattern; said lens projecting light from said light source in said pattern onto said surface to be inspected when said lens is facing said surface to highlight flaws and imperfections in said surface.

6. The lens as in claim 5 wherein:
   a) said narrow band of light produced from said optical wave guide is luminescent.

7. The lens as in claim 5 wherein:
   a) said narrow band of light produce by said optical wave guide is more intense than light projected by other portions of said lens.

8. The lens as in claim 5, wherein:
   a) said lens is mounted to a framework in front of said light source.

9. The lens as in claim 5, wherein:
   a) said dark colored area bleeds into said light colored area.

10. The lens as in claim 5, wherein:
    a) said light colored area is translucent; and
    b) said dark colored area is opaque.

11. A lens for use in association with a light source to inspect a surface for imperfections; said lens comprising:
    a) first and second face sections;
    b) an intermediate section formed from fluorescent plastic sheet material and extending between said first and second face sections such that an edge of said intermediate section forms a narrow band extending between said first and second face sections; and
    c) said lens having a dark colored area on said face sections through which said front edge of said intermediate section extends, and at least one light colored area adjacent said dark colored area.

12. The lens as in claim 11 wherein:
    a) said lens is mounted to a framework in front of said light source.

13. The lens as in claim 12 wherein:
    a) a portion of said intermediate section extends behind a rear surface of said first and second face sections of said lens.

14. The lens as in claim 11, wherein:
    a) said dark colored area bleeds into said light colored area.

15. The lens as in claim 11, wherein:
    a) said light colored area is translucent; and
    b) said dark colored area is opaque.

16. A light panel for inspecting a surface for imperfections; said panel comprising:
    a) a framework;
    b) a light source supported by said framework;
    c) a lens supported by said framework in front of said light source and comprising:
       i) first and second face sections;
       ii) an intermediate section formed from fluorescent plastic sheet material; said intermediate section extending between and transverse to said first and second face sections such that a front edge of said intermediate section extends flush with a front surface of said first and second face sections and a portion of said intermediate section extends behind a rear surface of said first and second face sections;
       iii) each of said first and second face sections includes an opaque dark colored band through which said front edge of said intermediate section extends and light colored bands extending adjacent said dark colored band.

17. The light panel as in claim 16 wherein:
    a) said lens is removably securable to said framework.

* * * * *